United States Patent
Foster et al.

(10) Patent No.: US 6,429,195 B1
(45) Date of Patent: *Aug. 6, 2002

(54) AQUEOUS PROLONGED RELEASE FORMULATION

(75) Inventors: Todd P. Foster, Kalamazoo; William M. Moseley, Augusta; James F. Caputo, Portage; Michael J. Hageman, Kalamazoo, all of MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/654,156

(22) Filed: Sep. 1, 2000

Related U.S. Application Data

(62) Division of application No. 08/766,563, filed on Dec. 13, 1996, now Pat. No. 6,150,330
(60) Provisional application No. 60/009,738, filed on Jan. 11, 1996.

(51) Int. Cl.⁷ .............................................. A61K 38/00
(52) U.S. Cl. .............................. 514/12; 514/2; 514/805; 530/399
(58) Field of Search .............................. 514/12, 2, 805; 530/399

(56) References Cited

U.S. PATENT DOCUMENTS

| | | | |
|---|---|---|---|
| 4,977,140 A | 12/1990 | Ferguson | 514/12 |
| 5,013,713 A | 5/1991 | Mitchell | 514/12 |
| 5,352,662 A | 10/1994 | Brooks | 514/12 |
| 5,756,458 A | 5/1998 | Kubiak et al. | 514/12 |
| 6,150,330 A | * 11/2000 | Foster et al. | 514/12 |

FOREIGN PATENT DOCUMENTS

| | | |
|---|---|---|
| WO | WO 90/15821 | 12/1990 |
| WO | WO 92/00095 | 1/1992 |
| WO | WO 94/06452 | 8/1993 |
| WO | WO 95/19787 | 7/1995 |

OTHER PUBLICATIONS

Carmona, P.; "Structural study of human growth hormone–releasing factor fragment (1–29) by vibrational spectroscopy";: Spectrochimica Acta, vol. 51A, No. 5, pp. 929–938 (1995).

Dahl, G.E., et al; "Galactopoietic Effects of a (1–30) $NH_2$ Analog of Growth Hormone–Releasing Factor in Dairy Cows;" Journal of Dairy Science, vol. 77, No. 9, pp. 2518–2525 (1994).

Mariette, Beatrice; "Release of the $GRF29NH_2$ analog of human $GRF44NH_2$ from a PLA/GA matrix", Journal of Controlled Release, vol. 24, pp. 237–246 (1993).

Pitt, C.G.; "The controlled parenteral delivery of polypeptides and proteins", International Journal of Pharmaceuticals, vol. 59, pp. 173–196 (1990).

Tucker, H.A., et al; "Long–term Somatotropic and Galactopoietic Effects of a (1–30) Ethyl Amide Analog of Growth Hormone–Releasing Factor"; Journal of Dairy Science, vol. 78, No. 7, pp. 1489–1497, (1995).

* cited by examiner

*Primary Examiner*—Dwayne C. Jones
*Assistant Examiner*—C. Delacroix-Muirheid
(74) *Attorney, Agent, or Firm*—James D. Darnley, Jr.; Thomas A. Cawley, Jr.

(57) ABSTRACT

Prolonged parenteral release into the circulatory system of a cow of a bioactive growth hormone releasing factor at desirably effective levels can be achieved using novel compositions in which the growth hormone releasing factor is present in an aqueous liquid at a dose of at least about 50 mg and at a concentration of at least about 20 mg/ml. Preferably, the growth hormone releasing factor is present in an aqueous liquid at a dose of about 200 mg and at a concentration of about 180 mg/ml. The aqueous bovine growth hormone releasing factor formulation provides for the sustained release of bovine somatotropin into the circulatory system of the animal for greater than seven (7) days.

4 Claims, 3 Drawing Sheets

AQUEOUS PROLONGED RELEASE FORMULATION

CROSS-REFERENCE TO RELATED APPLICATIONS

This application claims the benefit of the following provisional application: U.S. Serial No. 60/009,738, filed Jan. 11, 1996, under 35 USC 119(e)(i) and is a divisional of U.S. Ser. No. 08/766,563, filed Dec. 13, 1996, now U.S. Pat. No. 6,150,330.

BACKGROUND OF THE INVENTION

This invention relates to novel compositions useful for the sustained-release of bioactive proteins. More particularly, the present invention provides a superior aqueous sustained release injectable formulation of bovine growth hormone releasing factor. Also provided are methods of using these novel compositions for the sustained or prolonged release of bovine growth hormone releasing factor.

With the advent of genetic engineering, the large-scale availability of many bioactive peptides and proteins has been achieved. However, the administration of these recombinantly produced peptides and proteins presents a unique set of problems. In many cases the maintenance of the biological effect of these proteins requires long-term administration. Since daily administration of these agents is inconvenient, sustained or prolonged release is preferred.

For numerous reasons, the art has long focused on the use of biocompatible oils as vehicles to achieve the sustained release of many drugs, including proteins and specifically somatotropins. Among the patents directed to this technology are U.S. Pat. No. 5,013,713 to Mitchell and U.S. Pat. No. 4,977,140 to Ferguson et al. Mitchell reports that prolonged parenteral release of bovine somatotropin (bSt;BGH) at desirably effective levels can be achieved using substantially non-aqueous compositions comprising at least about 10% by weight of a biologically active somatotropin and, as a continuous phase of the composition, a biocompatible oil such as corn oil. Ferguson et al. report that the injection of a sustained release formulation comprising bSt, wax and an oil increases daily milk production in a cow for an extended period of time.

Those skilled in the art have also directed their attention to achieving the sustained release of other growth enhancing proteins such as growth hormone releasing factor. Specifically, U.S. Pat. No. 5,352,662 to Brooks et al. reports an injectable, extended release formulation which includes a growth hormone or a growth hormone releasing factor in a carrier including a biocompatible hydrophobic vehicle and an amount of polyglycerol ester effective to extend release of the proteins in the animal.

The above patents illustrate the art's emphasis on the use of non-aqueous delivery systems for the prolonged release of growth hormones and growth hormone releasing factors. Recently, the art has taught the use of an aqueous formulation to achieve the prolonged release of bSt. International Patent Application No. PCT/US95/00023 teaches the prolonged parenteral release into the circulatory system of a cow of a bioactive bSt. This is achieved by using novel compositions in which the bSt is present in an aqueous liquid at a dose of at least about 150 mg and at a concentration of at least about 50 mg/ml. The disclosed aqueous bSt formulation reportedly provides for the sustained release of bSt into the circulatory system of the animal for greater than 3 days.

Prior to this teaching, however, the art studiously avoided using aqueous systems for the sustained delivery of proteins, especially somatotropins. The reason for this behavior was the general view that proteins are highly unstable when exposed to aqueous environments for long periods of time. (Pitt, *Int. J. Pharmaceutics* 59:173–196 (1990)). As different proteins behave differently in aqueous environments (bSt comprises 191 amino acids whereas growth hormone releasing factors comprises 44 amino acids), the general view of the art that proteins are highly unstable when exposed to aqueous environments for long periods of time remains uncontradicted for growth hormone releasing factor.

INFORMATION DISCLOSURE

Mariette et al., *Journal of Controlled Release*, 24:237–246 (1993) report that release of $GRF29NH_2$ analog (comprised of the first 29 amino acids of human $GRF44NH_2$) from a compression molded matrix designed to form a percolating network of entrapped peptide particles depended much more on the solubility characteristics of the peptide than on the diffusion through the matrix or through the channels or on the morphology of the matrix itself. The authors report that controlled release was achieved in salt-containing media by using sink conditions generated by a continuous flow of $GRF29NH_2$-free aqueous media. The authors note that the $GRF29NH_2$ hGRF analog is also poorly soluble in plasma, but that phenomena in plasma appear rather complex and the peptide seemed to interact with serum proteins. The authors concluded by noting that further work was needed to better understand these interactions.

Carmona et al., *Spectrochimica Acta*, 51A(5):929–938 (1995) report that while the backbone of $GRF29NH_2$ is unordered in the solid state, some intermolecular beta-sheet aggregation is observed in aqueous solutions. They further report that their spectroscopic data indicate that the non-aggregated $GRF29NH_2$ analog exists as an ensemble of conformers in aqueous solution, that this peptide can undergo conformational changes on modification of the environment, and that such conformational flexibility of hGRF may be important for its clearance from circulation.

Pitt, *Int. J. Pharmaceutics* 59:173–196 (1990), reports on the difficulties in developing parenteral sustained release delivery systems for proteins such as the somatotropins which are highly unstable in aqueous environments at high protein concentrations.

U.S. Pat. No. 5,013,713 to Mitchell issued May 7, 1991, discloses a method for achieving prolonged release of a biologically active somatotropin into the circulatory system of an animal by the parenteral administration to the animal of a substantially non-aqueous composition of at least about 10% by weight of a biologically active somatotropin and, as a continuous phase of the composition, a biocompatible oil. Mitchell emphasizes that his composition should be non-aqueous in order not to accelerate release.

U.S. Pat. No. 4,977,140 to Ferguson et al. issued Dec. 11, 1990, discloses a method for obtaining 28 days of increased daily milk production from a dairy cow by injecting into the cow 2 to 10 grams of a formulation comprising 10–25% bovine somatotropin suspended in a carrier that comprises 8–20% of a wax and 80–92% of an oil. Ferguson et al. do not consider the question of whether aqueous formulations can be used as a prolonged release vehicles.

U.S. Pat. No. 5,352,662 to Brooks et al. issued Oct. 4, 1994, discloses an injectable, extended release formulation which includes a growth hormone or a growth hormone releasing factor in a carrier including a biocompatible hydrophobic vehicle and an amount of polyglycerol ester effective to extend release of the proteins in the animal. Brooks et al. do not consider the question of whether aqueous formulations can be used as a prolonged release vehicles.

International Application No. PCT/US95/00023 teaches the prolonged parenteral release into the circulatory system of a cow of a bioactive bSt using an aqueous formulation. This is achieved by using novel compositions in which the bSt is present in an aqueous liquid at a dose of at least about 150 mg and at a concentration of at least about 50 mg/ml. The disclosed aqueous bSt formulation reportedly provides for the sustained release of bSt into the circulatory system of the animal for greater than 3 days. The reference reveals nothing about whether an aqueous delivery system be used to achieve the prolonged release of growth hormone releasing factors.

SUMMARY OF THE INVENTION

The present invention discovered that substantially aqueous growth hormone releasing factor compositions can be used to achieve the prolonged release of a biologically active growth hormone releasing factor into the circulatory system of an animal by the parenteral administration to the animal of the substantially aqueous growth hormone releasing factor composition. The compositions comprise at least about 50 mg of a biologically active growth hormone releasing factor in an aqueous carrier at a concentration of at least about 20 mg/ml. The aqueous growth hormone releasing factor formulation provides for the sustained release of growth hormone releasing factor into the circulatory system of the animal for greater than about seven (7) days.

Preferably, the growth hormone releasing factor is present in an aqueous liquid at a dose of about 200 mg and at a concentration of about 180 mg/ml. At this dosage and concentration, the aqueous growth hormone releasing factor formulation provides for the sustained release of growth hormone releasing factor into the circulatory system of the animal for greater than about thirty-five (35) days.

The present invention thus provides extended release compositions which are highly effective and readily prepared. Further, this efficacy can be achieved in an injectable composition which does not require forcible compression of the growth hormone releasing factor with other materials to form solid implants. Further, treatments of the invention can be performed without incision, which for example is required with solid extended release implants. Additional embodiments, aspects and advantages of the invention will be apparent from the following description and appended claims.

DETAILED DESCRIPTION OF THE INVENTION

Figure 1:
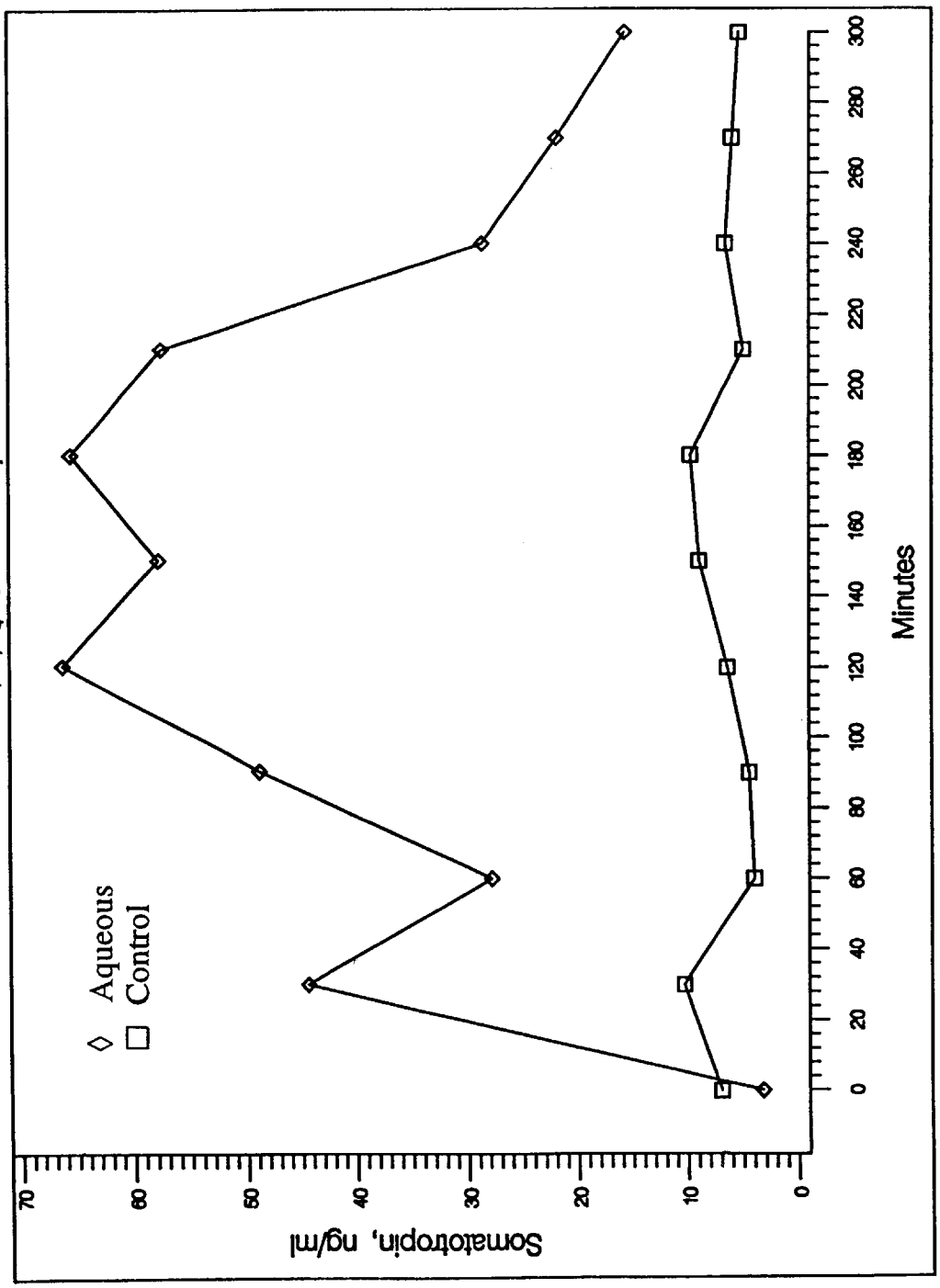
FIG. 1 illustrates the serum somatotropin (ST) mean concentrations in steers on the day of administration of the formulation.

For the purpose of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, a preferred embodiment of the invention provides, as a composition of matter, an injectable extended release formulation which includes a growth hormone releasing factor in an aqueous carrier. This formulation provides delivery of an efficacious dose of the hormone or releasing factor to the animal over prolonged periods of time following injection. The animal can be any species which produces endogenous growth hormones, including vertebrate species such as cattle, sheep, swine, goats, horses, birds, fish and humans.

The present invention is based on the discovery that effective extended release of growth hormone releasing factor (hereinafter "GRF", also commonly known as growth releasing factor, growth hormone releasing hormone, growth releasing hormone, and somatocrinin) can be achieved with an injectable formulation in which the GRF is in simple admixture with an aqueous carrier. As used herein, the term "in simple admixture" is intended to describe a condition in which the GRF/aqueous carrier formulation is an injectable paste providing extended release of the substance. As a result, the formulations of the invention are readily prepared.

The GRF to be utilized in the present invention can be any substance, of natural or synthetic origin, which exhibits the biological properties of a natural GRF. The natural GRF can be of any species, such as bovine, ovine, caprine, equine, porcine, avian, fish, human, and the like. Natural GRFs are extracted from the appropriate glandular tissue of animals; procedures for accomplishing this are known, albeit tedious. However, it is now well established practice to synthesize GRFs by the use of genetically modified microorganisms. It is oftentimes convenient or even preferred that such processes yield a modified GRF, that is, a substance that differs as to its structure from the naturally occurring GRF, but which retains the biological activity of the naturally occurring GRF. For example, a modified GRF may contain one or more additional amino acids, at one or both ends of the polypeptide chain; may have an amino acid sequence which differs from that of naturally occurring GRF; or may be an active fragment of naturally-occurring growth hormone releasing factor. For example, naturally occurring GRFs, pre-proteins of naturally occurring GRFs and fragments of naturally occurring GRFs (e.g. 29 amino acid growth hormone releasing factor) are known to cause elevation of growth hormone levels. Additional modifications will be understood by those skilled in the art. Therefore, the term "growth hormone releasing factor"(or "GRF") is used throughout this document to refer to both naturally occurring GRFs as well as synthetically produced substances which share the biological properties of naturally occurring GRFs, and which may be identical or which may vary as to structure.

As will be understood, the GRF can be provided in various physical forms. For instance, it can be a powder, e.g. air milled to decrease particle size, granules, etc. The injectable formulation will include an effective amount of GRF. Determining this amount is within the skill of the ordinary artisan. In the case of GRF, it is preferably included in an amount in the range of about 1% to about 18% by weight of the formulation.

The preferred overall formulations of the invention are syringeable, for example through a 14 gauge needle, and can be administered by injection into the subcutaneous space.

To promote a further understanding of the principles and advantages of the invention, the following examples are provided. It will be understood, however, that the following example is illustrative, and not limiting, of the invention.

EXAMPLE 1

FORMULATIONS/ADMINISTRATION

Twelve Holstein steers (250–300 kg) were weighed 7 days prior to trial initiation. Steers were ranked by weight from heaviest to lightest. Steers were divided into 2 blocks of 6 steers on the basis of weight. Treatments were assigned randomly within a block.

The treatment groups were designed to determine whether serum somatotropin (ST) could be sustained in steers when delivering growth hormone releasing factor analog (GRFA) dispersed in a highly concentrated aqueous paste. The treatment groups consisted of noninjected controls (CONT) and a 200 mg dose of 18% w/w GRFA in Sterile Water for Injection, USP (WAT-18). The GRF analog used has the following amino acid sequence [SEQ ID NO:1]:

```
Tyr-Ile-Asp-Ala-Ile-Phe-Thr-Ser-Ser-Tyr-
            5                   10

Arg-Lys-Val-Leu-Ala-Gln-Leu-Ser-Ala-Arg-
            15                  20

Lys-Leu-Leu-Gln-Asp-Ile-Leu-Ser-Arg-Homoserine-NHCH₂CH₃
            25                  30
```

The aqueous formulation was produced dispersing comminuted lyophilized GRFA in Sterile Water For Injection (SWFI, Vedco, Inc.) Because of rapid powder hydration during addition, powder incorporation was done by hand spatulation in a 50 mL beaker. One g of this viscous paste was immediately filled into each of six presterilized 3 mL syringes.

The area over the rib approximately 4 inches caudal to the axillary border of the scapula was clipped and the subcutaneous (SC) injection administered at this location. The aqueous paste formulations were delivered using a 14-gauge, 1.5 inch needle.

A cannula was inserted into the jugular vein at least one day prior to dosing. Blood (8 ml) was collected at 30 min intervals for 5 h beginning 7 h prior to feeding and ending 2 h prior to feeding on days 1, 3, 7, 14, 21, 28 and 35 following subcutaneous injection of the formulation. Additional samples at −40 and −20 min relative to formulation injection were collected on day 1.

ASSAYS/STATISTICS

The twelve Holstein steers were housed indoors in individual stalls (18–20° C.) and exposed to 16 hours light:8 hours darkness (lights on 0600) at The Upjohn Farms. Steers were trained to consume in a 2 hour period their entire daily rations offered once daily at 1500 hours. The daily ration consisted of 41.1% corn silage and 58.9% corn supplement/concentrate (B-382), on a dry matter basis, at a level to maintain 0.8–1.0 kg per head per day rate of gain. Water was available ad libitum. Research has shown that endogenous serum ST profile can be entrained to feeding (Moseley et al. (1988) *J. Endocr.* 117:253–259). Thus, the blood sampling regimen was scheduled with relationship to feeding such that the ability to characterize the temporal ST pattern was optimized. Serum obtained were assayed for ST concentration by radioimmunoassay (Moseley et al. (1982) *J. Anim. Sci.* 55:1062–1070).

The formulations' effectiveness were evaluated by calculating area under the ST response curve (AUC) for each sampling day determined by trapezoidal summation, summed daily ST-AUC, maximum ST concentrations over all sampling periods, time maximum ST occurred and time of return of mean ST-AUC for each sample day to mean control ST-AUC. The a priori hypotheses was tested at a significance level of 0.05. Maximum overall ST concentrations and AUC were analyzed using analysis of variance for a randomized complete block design, with blocks (weight groups) as a random effect (Steel, R. G. D. and J. H. Torrie (1980) *Principles and Procedures of Statistics*, McGraw-Hill Book, Co., New York). Daily areas under the curve were analyzed by mixed models of variance analysis (SAS Procedure MIXED). If the treatment by sampling period interaction was significant, treatment difference was examined at each sampling period (Milliken, G. A. and D. E. Johnson (1984) *Analysis of Messy Data*, Van Nostrand Reinhold, N.Y., pp. 19–22). A least significant difference (LSD) was calculated to compare treatment means at a given time using weighted estimates of treatment x block and residual variances and a Satterthwaite approximation of the degrees of freedom as described by Milliken and Johnson, supra. Confidence intervals (95%) were constructed around the control means at each time using the LSD. Levene's test for homogeneity of variance was used prior to all analyses of variance. Data with heterogeneous variance were transformed using $\log_{10}$. All analysis were performed using SAS (1989) *SAS User's Guide: Statistics. Version 6.* SAS Institute, Cary, N.C.

RESULTS

A. Serum ST Concentrations

Figure 2:
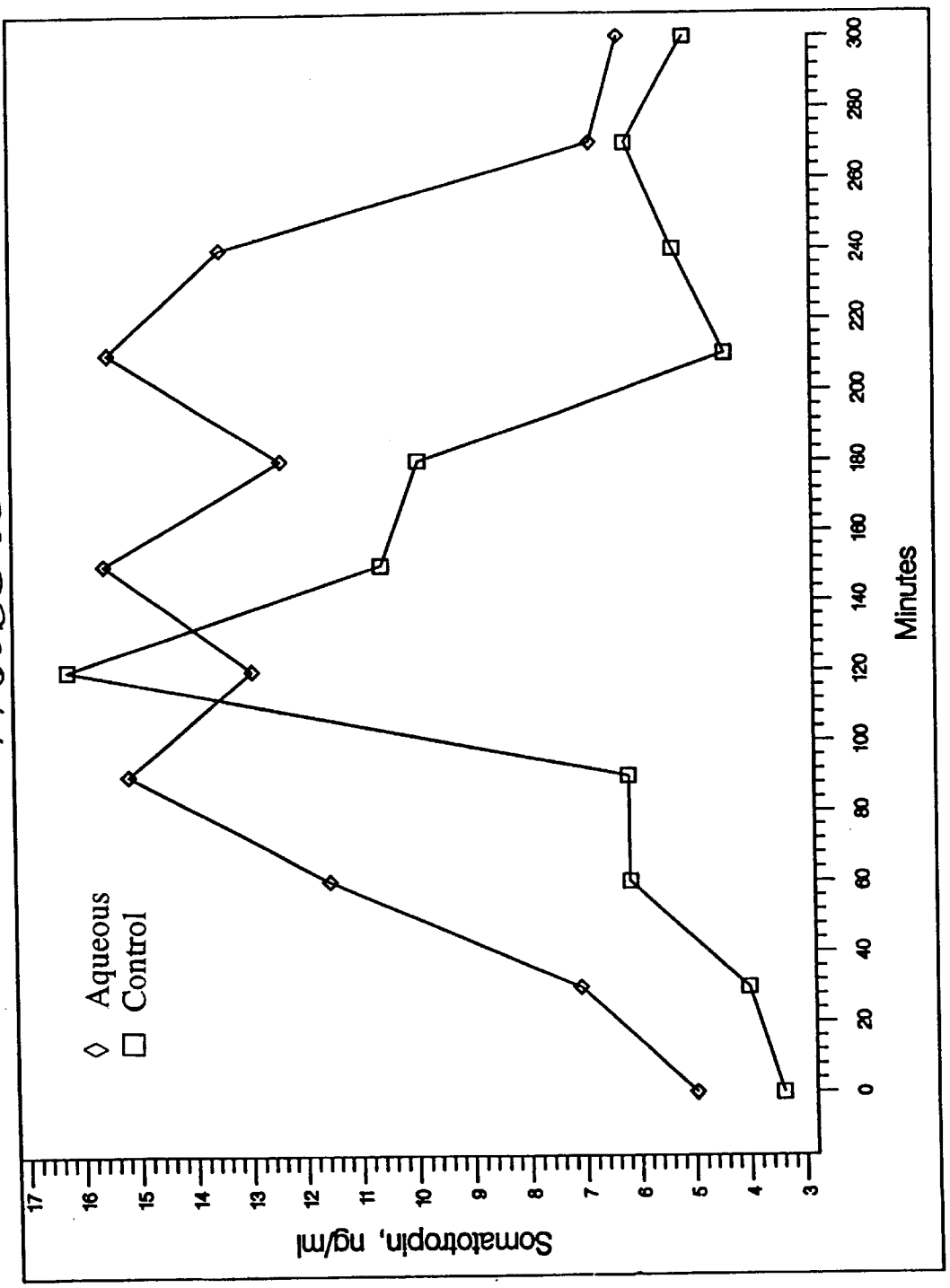
FIG. 2 illustrates the serum ST mean concentrations in steers 35 days after administration of the formulation.

The mean concentration of serum ST observed in steers receiving the aqueous formulation or no formulation at days 1 and 35 are shown in FIGS. 1 and 2, respectively. These data along with concentrations found on days 3, 7, 14, 21 and 28 were used to calculated the daily ST-AUC. For animals receiving the aqueous formulation the maximum mean serum ST (121.4 ng/mL) and time when this maximum occurred (6.5 days) is shown in Table 1. The maximum concentration was greater (P<0.05) than the controls 38.4 ng/mL and the time when this maximum occurred was different than controls.

B. Area Under The ST Curve

Figure 3:
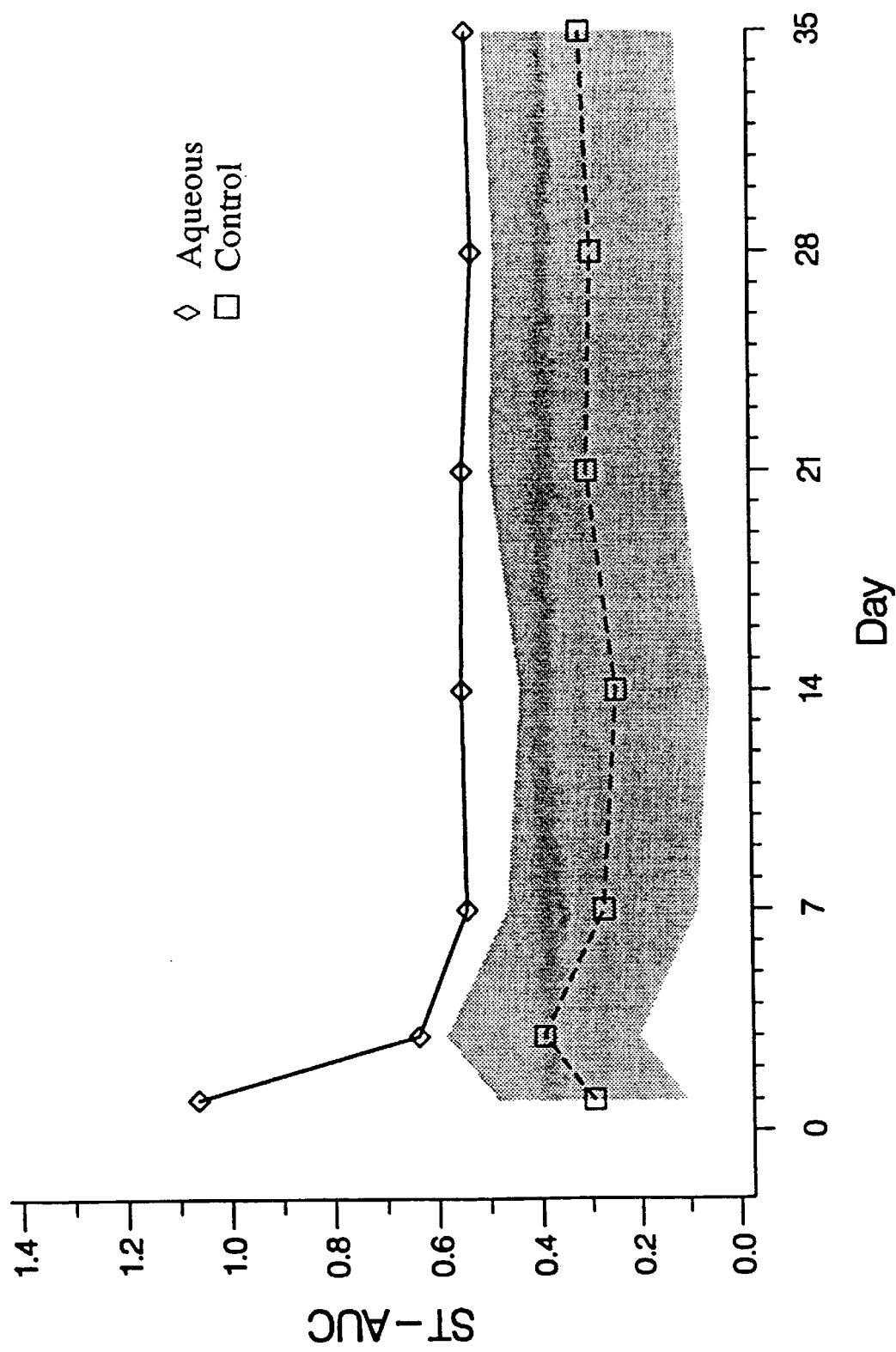
FIG. 3 illustrates the treatment group daily somatotropin-area under curve (ST-AUC) with 95% confidence interval constructed around daily control group means.

The daily ST-AUC were calculated for days 1, 3, 7, 14, 21, 28, and 35. Heterogeneity of variance (Levene's test) was observed so data were transformed to $\log_{10}$. The least square means of daily serum ST-AUC for the aqueous treatment and control groups are shown in Table 2. The overall control mean was 0.299 units as determined by averaging the area for the control steers over all sampling days. This control average was compared to the aqueous treatment group to determine when daily ST-AUC returned to baseline. The comparison is shown in FIG. 3. There was still a difference between control and the WAT-18 group at day 35 when the study was completed.

The total serum ST-AUC in Holstein steers over 35 days after receiving WAT-18 or no U-90699F is shown in Table 1. The least square means for total ST-AUC were 14.9 (CONT) and 36.2 units (WAT-18). The steers receiving the aqueous formulation had greater (P<0.05) total ST-AUC than control steers.

The main outcome measured by the experiment was the time treatment ST-AUC were elevated above controls. A long duration was achieved with an aqueous formulation. By ratioing the treatment ST-AUC to the daily average ST-AUC (0.299 units) it was observed that on day one the aqueous formulation. ST-AUC was 3.55 times greater than the mean control ST-AUC. By day 7 this had decreased to 1.81 times greater. The ST-AUC stayed between 1.74 to 1.83 times greater than control between days 7 to 35 implying zero-order release.

TABLE 1

Measured Parameters

| Treatment | Mean Maximum ST Concentration (ng/mL) | Time When Mean Maximum ST Concentrations Occurred (days) | Total-AUC (units) |
|---|---|---|---|
| CONTROL | 38.4[a] | 15.7[b] | 14.9[a] |
| WAT-18 | 121.4[b] | 6.5[a] | 36.2[b] | a,b Means within a column with a common superscript are not different, P < 0.05.

TABLE 2

Area Under the ST Curve ($\log_{10}$) for the Treatment Groups[1]

| Day | CONTROL | WAT-18 |
|---|---|---|
| 1 | 0.294 | 1.063 |
| 3 | 0.392 | 0.635 |
| 7 | 0.272 | 0.540 |
| 14 | 0.244 | 0.546 |
| 21 | 0.298 | 0.542 |
| 28 | 0.287 | 0.520 |
| 35 | 0.307 | 0.529 |

[1]Significantly difference was observed through 35 days, P < 0.05, LSD = 0.1885.

SEQUENCE LISTING

```
<160> NUMBER OF SEQ ID NOS: 1

<210> SEQ ID NO 1
<211> LENGTH: 30
<212> TYPE: PRT
<213> ORGANISM: Artificial Sequence
<220> FEATURE:
<223> OTHER INFORMATION: GRF analog
<220> FEATURE:
<221> NAME/KEY: MISC_FEATURE
<222> LOCATION: (1)..(30)
<223> OTHER INFORMATION: Xaa is defined as t he amino acid Homoserine.

<400> SEQUENCE: 1

Tyr Ile Asp Ala Ile Phe Thr Ser Ser Tyr A rg Lys Val Leu Ala Gln
1               5                   10                  15

Leu Ser Ala Arg Lys Leu Leu Gln Asp Ile L eu Ser Arg Xaa
            20                  25                  30
```

We claim:

1. A method for achieving enhanced concentrations of endogenous somatotropin in the circulatory system of an animal of greater than seven (7) days which comprises parenteral administration to the animal of a substantially aqueous bovine growth hormone releasing factor composition comprising at least about 50 mg of a biologically active bovine growth hormone releasing factor in water at a concentration of at least about 20 mg/ml.

2. A pharmaceutical composition comprising at least about 200 mg of a biologically active bovine growth hormone releasing factor in water at a concentration of at least about 180 mg/ml to form a syringeable aqueous bovine growth hormone releasing factor solution, said solution being substantially void of absorption modifying agents and buffering agents.

3. A method for achieving enhanced concentrations of endogenous somatotropin in the circulatory system of an animal of greater than thirty-five (35) days which comprises parenteral administration to the animal of a substantially aqueous bovine growth hormone releasing factor composition comprising at least about 200 mg of a biologically active bovine growth hormone releasing factor in water at a concentration of at least about 180 mg/ml.

4. A pharmaceutical composition comprising at least about 50 mg of a biologically active bovine growth hormone releasing factor in water at a concentration of at least about 20 mg/ml to form a syringeable aqueous bovine growth hormone releasing factor solution, said solution being substantially void of absorption modifying agents and buffering agents.

* * * * *